US012690896B2

(12) United States Patent
Biedermann et al.

(10) Patent No.: US 12,690,896 B2
(45) Date of Patent: Jul. 28, 2026

(54) COUPLING ASSEMBLY FOR COUPLING A ROD TO A BONE ANCHORING ELEMENT, AND POLYAXIAL BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/349,055

(22) Filed: Oct. 3, 2025

(65) Prior Publication Data

US 2026/0026848 A1 Jan. 29, 2026

Related U.S. Application Data

(63) Continuation of application No. 19/210,212, filed on May 16, 2025, now Pat. No. 12,433,645, which is a
(Continued)

(30) Foreign Application Priority Data

Jan. 13, 2014 (EP) ..................................... 14151009

(51) Int. Cl.
*A61B 17/70* (2006.01)

(52) U.S. Cl.
CPC ...... *A61B 17/7037* (2013.01); *A61B 17/7032* (2013.01)

(58) Field of Classification Search
CPC ............ A61B 17/7032; A61B 17/7034; A61B 17/7035; A61B 17/7037; A61B 17/7038
See application file for complete search history.

(56) References Cited

U.S. PATENT DOCUMENTS

| | | | |
|---|---|---|---|
| 5,466,237 A | 11/1995 | Byrd, III et al. | |
| 5,624,442 A | 4/1997 | Mellinger et al. | |

(Continued)

FOREIGN PATENT DOCUMENTS

| | | |
|---|---|---|
| CN | 101455580 A | 6/2009 |
| CN | 102475572 A | 5/2012 |
| EP | 2 659 845 A1 | 11/2013 |

OTHER PUBLICATIONS

Partial European Search Report issued by the EPO for EP 14151009.9 on May 27, 2014 (5 pages).

(Continued)

*Primary Examiner* — Eric S Gibson
(74) *Attorney, Agent, or Firm* — Womble Bond Dickinson (US) LLP

(57) ABSTRACT

A coupling assembly for coupling a rod to a bone anchoring element, including a receiving part having first and second ends, a recess at the first end for the rod, and an accommodation space for a head of the bone anchoring element, the accommodation space having an opening at the second end to permit insertion of the head into the receiving part, a retainer element configured to be arranged at least partially in the accommodation space and to hold at least part of the head, and a spring element configured to be arranged at least partially in the accommodation space and to be compressed in an axial direction. The retainer element and the spring element are separate parts. When the retainer element and the spring element are in the accommodation space of the receiving part in a first position, the spring element extends into the recess of the receiving part.

12 Claims, 13 Drawing Sheets

Related U.S. Application Data continuation of application No. 18/439,562, filed on Feb. 12, 2024, now Pat. No. 12,324,608, which is a continuation of application No. 17/376,900, filed on Jul. 15, 2021, now Pat. No. 11,925,391, which is a continuation of application No. 16/989,366, filed on Aug. 10, 2020, now Pat. No. 11,090,090, which is a continuation of application No. 15/900,204, filed on Feb. 20, 2018, now Pat. No. 10,779,862, which is a continuation of application No. 14/596,169, filed on Jan. 13, 2015, now Pat. No. 9,924,971.

(56) References Cited

U.S. PATENT DOCUMENTS

| | | | | |
|---|---|---|---|---|
| 7,250,052 | B2 * | 7/2007 | Landry | A61B 17/7085 606/86 A |
| 8,075,603 | B2 | 12/2011 | Hammill et al. | |
| 8,353,932 | B2 * | 1/2013 | Jackson | A61B 17/702 606/246 |
| 8,444,681 | B2 * | 5/2013 | Jackson | A61B 17/7091 606/305 |
| 8,870,930 | B2 | 10/2014 | Carbone et al. | |
| 9,198,695 | B2 * | 12/2015 | Shluzas | A61B 17/70 |
| 9,636,148 | B2 * | 5/2017 | Shluzas | A61B 17/70 |
| 9,924,971 | B2 * | 3/2018 | Biedermann | A61B 17/7037 |
| 10,779,862 | B2 * | 9/2020 | Biedermann | A61B 17/8888 |
| 11,090,090 | B2 * | 8/2021 | Biedermann | A61B 17/8888 |
| 11,925,391 | B2 * | 3/2024 | Biedermann | A61B 17/7037 |
| 12,324,608 | B2 * | 6/2025 | Biedermann | A61B 17/7037 |
| 12,433,645 | B2 * | 10/2025 | Biedermann | A61B 17/8615 |
| 2004/0138662 | A1 * | 7/2004 | Landry | A61B 17/861 606/279 |
| 2004/0143265 | A1 * | 7/2004 | Landry | A61B 17/701 606/279 |
| 2004/0172022 | A1 * | 9/2004 | Landry | A61B 17/701 606/279 |
| 2004/0267264 | A1 * | 12/2004 | Konieczynski | A61B 17/7032 606/289 |
| 2006/0084993 | A1 * | 4/2006 | Landry | A61B 17/7032 606/279 |
| 2006/0100621 | A1 * | 5/2006 | Jackson | A61B 17/7032 606/306 |
| 2006/0100622 | A1 * | 5/2006 | Jackson | A61B 17/8625 606/301 |
| 2006/0142761 | A1 * | 6/2006 | Landry | A61B 17/1703 606/86 A |
| 2007/0161996 | A1 * | 7/2007 | Biedermann | A61B 17/7037 606/305 |
| 2007/0219554 | A1 * | 9/2007 | Landry | A61B 17/7035 623/17.16 |
| 2007/0270813 | A1 * | 11/2007 | Garamszegi | A61B 17/7032 606/278 |
| 2007/0270831 | A1 * | 11/2007 | Dewey | A61B 17/7038 606/86 A |
| 2008/0077139 | A1 * | 3/2008 | Landry | A61B 17/7085 606/103 |
| 2009/0005814 | A1 * | 1/2009 | Miller | A61B 17/7085 606/301 |
| 2009/0163956 | A1 | 6/2009 | Biedermann et al. | |
| 2010/0030279 | A1 | 2/2010 | Flynn et al. | |
| 2010/0160974 | A1 * | 6/2010 | Viker | A61B 17/866 606/301 |
| 2010/0262196 | A1 * | 10/2010 | Barrus | A61B 17/7037 606/308 |
| 2011/0004256 | A1 * | 1/2011 | Biedermann | A61B 17/864 606/86 R |
| 2011/0009911 | A1 * | 1/2011 | Hammill, Sr. | A61B 17/7038 606/308 |
| 2012/0059426 | A1 * | 3/2012 | Jackson | A61B 17/68 606/305 |
| 2012/0143265 | A1 | 6/2012 | Biedermann et al. | |
| 2012/0177462 | A1 * | 7/2012 | Fritzinger | A61B 17/861 411/413 |
| 2012/0209335 | A1 | 8/2012 | Termyna et al. | |
| 2012/0209336 | A1 * | 8/2012 | Jackson | A61B 17/7082 606/305 |
| 2013/0046350 | A1 | 2/2013 | Jackson et al. | |
| 2013/0096620 | A1 * | 4/2013 | Biedermann | A61B 17/70 606/279 |
| 2013/0131734 | A1 | 5/2013 | Longtain et al. | |
| 2013/0150852 | A1 * | 6/2013 | Shluzas | A61B 17/7032 606/65 |
| 2013/0338721 | A1 * | 12/2013 | Biedermann | A61B 17/7034 606/305 |
| 2013/0345758 | A1 * | 12/2013 | Biedermann | A61B 17/7037 606/279 |
| 2014/0188174 | A1 * | 7/2014 | Biedermann | A61B 17/8625 606/305 |
| 2014/0236239 | A1 * | 8/2014 | Biedermann | A61B 17/7037 606/278 |
| 2014/0321945 | A1 * | 10/2014 | Black | F16B 29/00 411/383 |
| 2015/0142059 | A1 * | 5/2015 | Biedermann | A61B 17/7037 606/266 |
| 2015/0196337 | A1 * | 7/2015 | Biedermann | A61B 17/7032 606/305 |
| 2015/0196338 | A1 * | 7/2015 | Biedermann | A61B 17/8605 606/305 |
| 2015/0250512 | A1 * | 9/2015 | Poker | A61B 17/7037 606/305 |
| 2016/0045229 | A1 * | 2/2016 | Shluzas | A61B 17/7001 29/446 |
| 2016/0262803 | A1 * | 9/2016 | Nelson | A61B 17/7032 |
| 2016/0331412 | A1 * | 11/2016 | Biedermann | A61B 17/7037 |
| 2017/0100164 | A1 * | 4/2017 | Landry | A61B 17/861 |
| 2018/0235666 | A1 * | 8/2018 | Biedermann | A61B 17/8615 |
| 2021/0022774 | A1 * | 1/2021 | Biedermann | A61B 17/8888 |
| 2022/0000522 | A1 * | 1/2022 | Biedermann | A61B 17/7032 |
| 2024/0261000 | A1 * | 8/2024 | Biedermann | A61B 17/7037 |
| 2025/0275788 | A1 * | 9/2025 | Biedermann | A61B 17/8888 |

OTHER PUBLICATIONS

Extended European Search Report and Opinion issued by the EPO for EP 14151009.9 on Aug. 19, 2014 (10 pages).

* cited by examiner

1

COUPLING ASSEMBLY FOR COUPLING A ROD TO A BONE ANCHORING ELEMENT, AND POLYAXIAL BONE ANCHORING DEVICE

CROSS-REFERENCE TO RELATED APPLICATIONS

This application is a continuation of U.S. patent application Ser. No. 19/210,212, filed May 16, 2025, which is a continuation of U.S. patent application Ser. No. 18/439,562, filed Feb. 12, 2024, now U.S. Pat. No. 12,324,608, which is a continuation of U.S. patent application Ser. No. 17/376,900, filed Jul. 15, 2021, now U.S. Pat. No. 11,925,391, which is a continuation of U.S. patent application Ser. No. 16/989,366, filed Aug. 10, 2020, now U.S. Pat. No. 11,090,090, which is a continuation of U.S. patent application Ser. No. 15/900,204, filed Feb. 20, 2018, now U.S. Pat. No. 10,779,862, which is a continuation of U.S. patent application Ser. No. 14/596,169, filed Jan. 13, 2015, now U.S. Pat. No. 9,924,971, which claims the benefit of U.S. Provisional Patent Application Ser. No. 61/926,683, filed Jan. 13, 2014, the contents of which are hereby incorporated by reference in their entirety, and claims priority from European Patent Application EP 14151009.9, filed Jan. 13, 2014, the contents of which are hereby incorporated by reference in their entirety.

BACKGROUND

Field

The invention relates to a coupling assembly for coupling a rod to a bone anchoring element and to a polyaxial bone anchoring device with such a coupling assembly. The coupling assembly includes a receiving part with a channel for receiving the rod, an accommodation space for accommodating a head of a bone anchoring element and a retainer element for retaining the head of the bond anchoring element in the receiving part. Furthermore, a spring element is provided that is biased in such a manner that the retainer element snaps automatically onto the head of the bone anchoring element when the head is being inserted.

Description of Related Art

From US 2013/0150852 A1, a polyaxial bone anchor including a housing, a bone screw, and a retainer for pivotably coupling the head of the bone screw to the housing is known. The retainer is positioned into the bore of the housing and includes a plurality of alternating tabs and slots circumferentially arranged to define a cavity for receiving the head portion of the bone screw therein. The bone anchor further includes a resilient spring means biasing the retainer towards the lower end of the housing. The head portion of the bone screw may apply a force against the retainer opposing and overcoming the biasing force of the resilient spring means. The resilient spring means may be, for example, a wave washer, a helical spring, an elastomeric member etc. or may be circumferential or helical slots formed in the retainer.

U.S. Pat. No. 8,075,603 B2 describes a fastening system consisting of a polyaxial ball and socket joint used in conjunction with a bone screw having threads on one end and a spherical connector on the other end operating as a pivot point about which a connection assembly moves in a polyaxial fashion. A substantially U-shaped connecting assembly has a lower receptacle that operates as a socket for housing an upper retainer ring and a lower split retainer ring. The socket is receptive to the spherical connector which is inserted through the lower split retainer ring causing a momentary displacement thereof which allows for the positioning of the spherical connector between the upper and lower retainer rings. A resilient component, such as two helical springs, positioned between the upper retainer ring and the connecting assembly permits relative predetermined placement and retention of the spherical connector relative to the connector assembly.

SUMMARY

The above polyaxial bone anchors allow for inserting a spherical head of a bone screw into a receiver by pushing the head against a spring force of a resilient member. However, there is still a need for a coupling assembly and a polyaxial bone anchor with such a coupling assembly that is improved with regard to several aspects, such as the efficiency and safety of the coupling.

It is an object of the invention to provide a coupling assembly for coupling a rod to a bone anchoring element, and a polyaxial bone anchor comprising such a coupling assembly, that provides a safe connection of the bone anchoring element to the coupling assembly with a low insertion force, while also providing a high retention force, and where only a small amount of axial travel or displacement is needed to insert the bone anchoring element into the coupling assembly. Also, the coupling assembly can be easier to manufacture.

The coupling assembly includes a receiving part with an accommodation space for accommodating the head of the bone anchoring element and a retainer element configured to be positioned at least partially in the accommodation space. Further, the coupling assembly includes a spring element in the form of, for example, a compression spring that is compressible in an axial direction and that fully extends around the central axis in a circumferential direction and that has an axial length so that it can be engaged by an inserted rod. Preferably, the spring element is a wave spring element, which can generate a higher spring force on a given axial length compared to other spring elements. Therefore, the snap-over of the retainer element on the head of the bone anchoring element is facilitated.

The retainer element further may have at least one horizontal slit at its bottom end that may only need a low insertion force to insert the head into the receiving part. Simultaneously, a retention force that holds the head in the receiving part is high compared to the insertion force. Therefore, the bone anchoring element is effectively prevented from being pulled-out from the lower opening. In addition, because of the small or short insertion path, occurrences of milling under the head or sticking out of the head from the bone can be avoided or reduced.

The coupling assembly may further include a pressure element for exerting pressure onto the head of the bone anchoring element to lock the bone anchoring element in a specific angular position relative to the receiving part. The retainer element may encompass at least a portion of the pressure element from an outer side thereof, so that increasing a height of the receiving part for accommodating both the retainer element and the pressure element may not be necessary. Hence, a low profile implant can be provided.

In addition, the receiving part is monolithic and sized such that the retainer element and the spring element, as well as the pressure element, can be mounted from the top opening thereof.

The pressure element may be held in a position such that the head of the bone anchoring element is held by a frictional force exerted by the pressure element onto the head. The frictional force may be such that the head can still be pivoted by applying a force to overcome the frictional force.

The coupling assembly can be assembled in situ with a bone anchoring element that has been already inserted into a bone or a vertebra.

The head of the bone anchoring element may have at its free end an engagement recess for a driver that comprises a groove shaped and arranged in a spiral-like manner. This allows for transmission of high torques onto the bone anchoring element. Furthermore, the free end surface of the anchoring element that has the drive recess may have a spherical shape. In an embodiment where the rod presses directly onto the head without using a pressure element, the spherical shape ensures that a necessary or sufficient contact area between the rod and the head is provided, even at large pivot angles of the bone anchoring element.

With a coupling assembly according to embodiments of the invention, a modular polyaxial bone anchoring device can be provided that may include several bone anchoring elements that differ with respect to the length of the shank, anchoring features of the shank, such as different thread types and/or thread pitches, different diameters of the shank, and/or with respect to the shank being cannulated or non-cannulated, among other features.

BRIEF DESCRIPTION OF THE DRAWINGS

Further features and advantages of the invention will become more apparent from the description of various embodiments using the accompanying drawings. In the drawings.

DETAILED DESCRIPTION

Figures 1, 2:
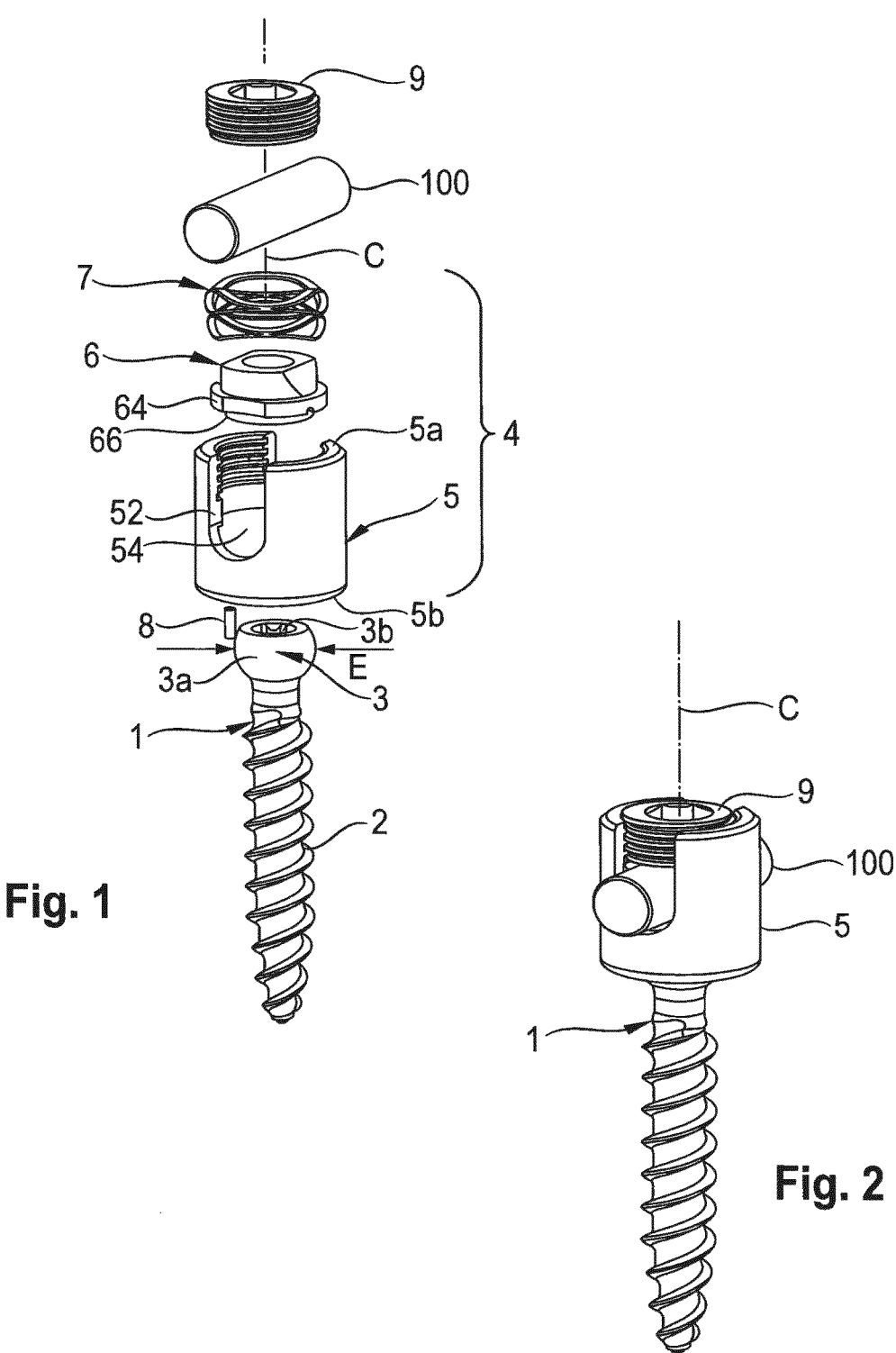
FIG. 1 shows a perspective exploded view of a first embodiment of a bone anchoring device.
FIG. 2 shows a perspective view of the bone anchoring device of FIG. 1 in an assembled state.
Figures 3, 4, 5, 6:
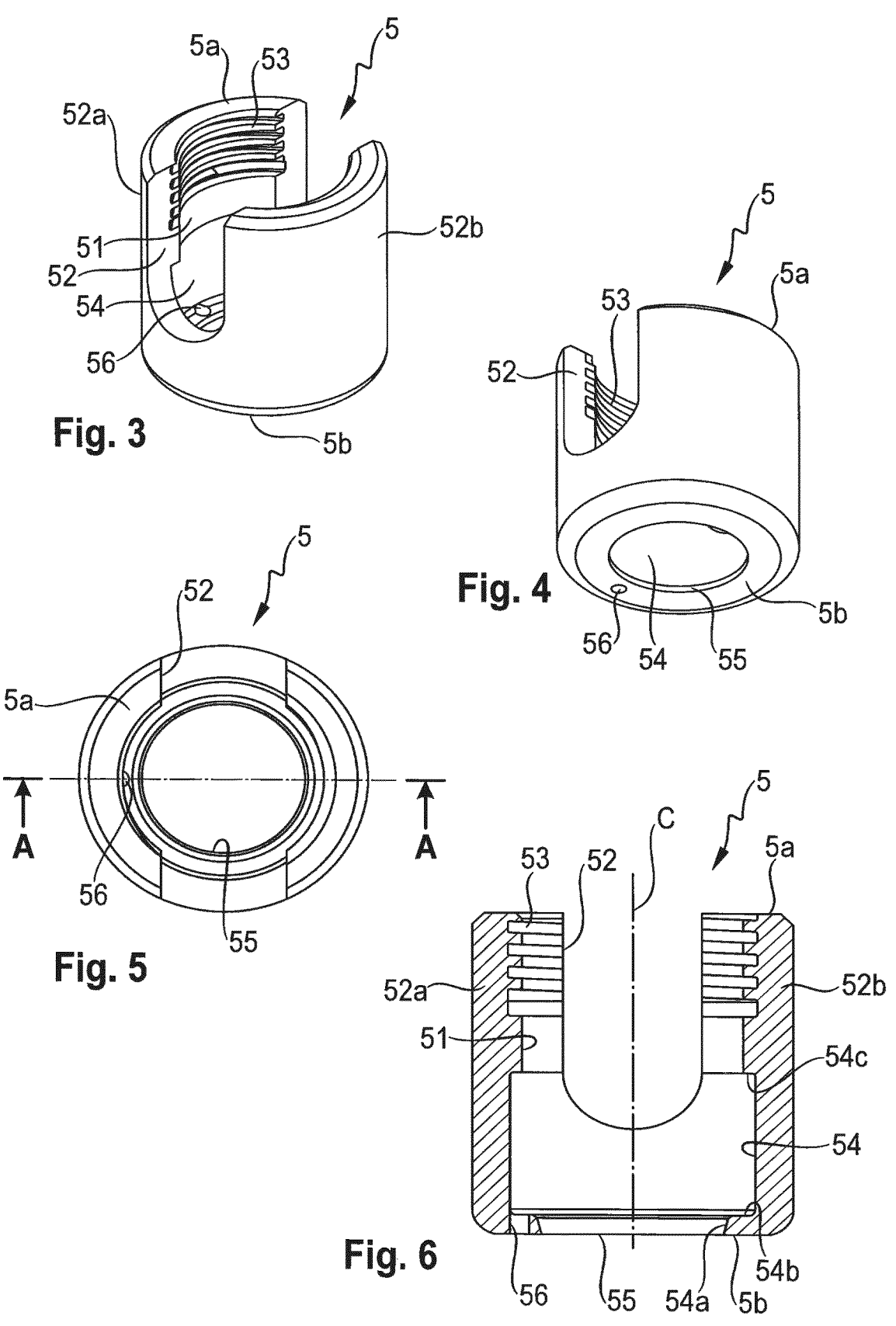
FIG. 3 shows a perspective view from above of a receiving part according to the first embodiment.
FIG. 4 shows a perspective view from the bottom of a receiving part shown in FIG. 3.
FIG. 5 shows a top view of the receiving part shown in FIGS. 3 and 4.
FIG. 6 shows a cross-sectional view of the receiving part shown in FIGS. 3 to 5, the cross-section being taken along line A-A in FIG. 5.

As shown in FIGS. 1 and 2, a bone anchoring device according to a first embodiment includes a bone anchoring element 1 in the form of a bone screw having a threaded shank 2 and a head 3. The head 3 has a spherical segment-shaped outer surface portion 3*a*, including a greatest outer diameter E of the sphere, and a free end with a recess 3*b* for engagement with a screwing-in tool. The bone anchoring device further includes a coupling assembly 4 for coupling a stabilization rod 100 to the bone anchoring element 1. The coupling assembly 4 includes a receiving part 5, and a retainer element 6 and a spring element 7 configured to be arranged in the receiving part 5. A pin 8 may be provided for securing the retainer element 6 against rotation in the receiving part 5.

In addition, a locking element 9 in the form of an inner screw is provided for securing the rod 100 in the receiving part 5 and for locking the whole device.

Referring in particular to FIGS. 3 to 6, the receiving part 5 is a monolithic part that is substantially cylindrical and has a first end or top end 5*a*, a second end or bottom end 5*b*, and a central axis of symmetry C passing through the top end 5*a* and the bottom end 5*b*. A bore 51 is provided that is coaxial with the central axis C. In a first region adjacent to the top end 5*a*, the receiving part 5 has a substantially U-shaped recess 52 with a bottom directed towards the bottom end 5*b*, and two free lateral legs 52*a*, 52*b* extending towards the top end 5*a*. On the legs 52*a*, 52*b*, an internal thread 53 is provided that cooperates with the locking element 9. The channel formed by the U-shaped recess 52 is sized so as to receive the rod 100 therein for connecting two or more bone anchoring devices. In a region that extends from a distance above (i.e., closer to the top end 5*a* than) the bottom of the U-shaped recess 52 to a distance from the bottom end 5*b*, the bore 51 has a greater diameter compared to other portions of the bore 51 so that an accommodation space 54 is formed to receive the head 3 of the bone anchoring element 1 and to receive the retainer element 6 as well as the spring element 7. The accommodation space 54 has, at its lower end adjacent to the bottom end 5*b* of the receiving part, a seat portion 54*a* for the retainer element 6. The seat portion 54*a* has a smaller diameter than the main portion of the accommodation space 54 and conically tapers toward the bottom end 5*b* of the receiving part 5. Between the seat portion 54*a* and the rest of the accommodation space 54, a shoulder 54*b* is provided that may also function as a stop for the retainer element 6. An upper edge 54*c* between the accommodation space 54 and the rest of the bore 51 forms a stop for the spring element 7.

The accommodation space 54 further has an opening 55 at the bottom end 5*b*, the inner diameter of which is larger than the greatest outer diameter E of the head 3 of the bone anchoring element 1, so that the head 3 can be inserted from the bottom end 5*b*. The edge or perimeter surrounding the opening 55 has a through-hole 56 that extends into the accommodation space 54 and that serves as a press-fit accommodation of the pin 8. An axis of the through-hole 56 may be parallel to the central axis. The through-hole 56 of the receiving part 5 is positioned in a circumferential direction approximately corresponding to a center of one of the legs 52*a*, 52*b*.

Referring more in detail to FIGS. 7 to 10, the retainer element 6 will be explained. The retainer element 6 resembles a cap-like part, and includes a first end or top end 6*a* and an opposite second end or bottom end 6*b*. Adjacent to the bottom end 6*b*, a spherical segment-shaped recess 61 extends into the retainer element 6 with an inner diameter that matches an outer diameter of the spherical surface portion 3*a* of the head 3. The extension of the recess 61 in an axial direction is such that when the head 3 is inserted into the recess 61, the bottom end 6*b* extends below (i.e., closer to the shank 2 than) the region of the head 3 with the greatest diameter E.

A coaxial bore 62 extends from the top end 6*a* into the recess 61 to allow access to the head 3 of the anchoring element 1 with a tool. An outer surface of the retainer element 6 has a first portion 63 adjacent to the top end 6*a* that is substantially conically shaped and that tapers and narrows towards the first end 6*a*. The first portion 63 may have two opposite flattened sides 63*a* that facilitate gripping the retainer element 6 with a tool (now shown) for assembling the retainer element 6 and the receiving part 5.

Figures 14, 15, 16:
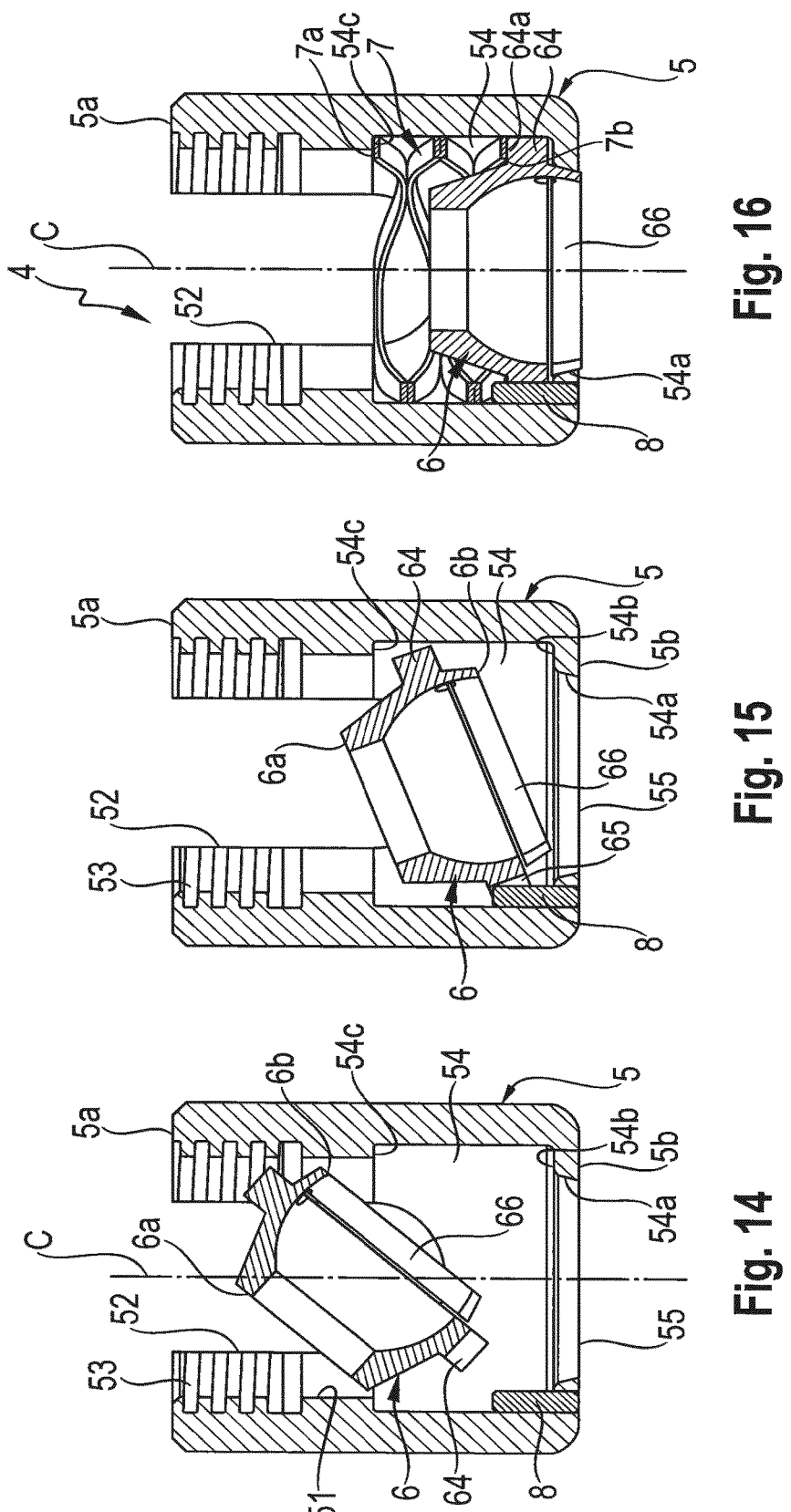
FIGS. 14 and 15 show cross-sectional views illustrating steps of mounting the retainer element to the receiving part according to the first embodiment.
FIG. 16 shows a cross-sectional view of a fully assembled coupling assembly according to the first embodiment, with the retainer element and the spring element, the cross-section being taken in a direction transverse to an axis of a channel for the rod.

Approximately in the region with the largest inner diameter of the recess 61, an outwardly protruding annular edge 64 is formed with a maximum outer diameter that is only slightly smaller than an inner diameter of the accommodation section 54 of the receiving part 5, as shown, for example, in FIG. 16. The outwardly protruding annular edge 64 has an upper side 64*a* that is configured to support the spring element 7. Flattened portions 64*b* of the annular edge 64 are provided and arranged at substantially 90° with respect to the flattened portions 63*a* of the first portion 63. On one side at substantially 90° with respect to the flattened portions 64*b* in a circumferential direction, a substantially U-shaped recess 65 is provided in the outer surface of the annular edge 64 which extends in an axial direction. The recess 65 is configured to receive the pin 8 therein.

Figures 7, 8, 9, 10:
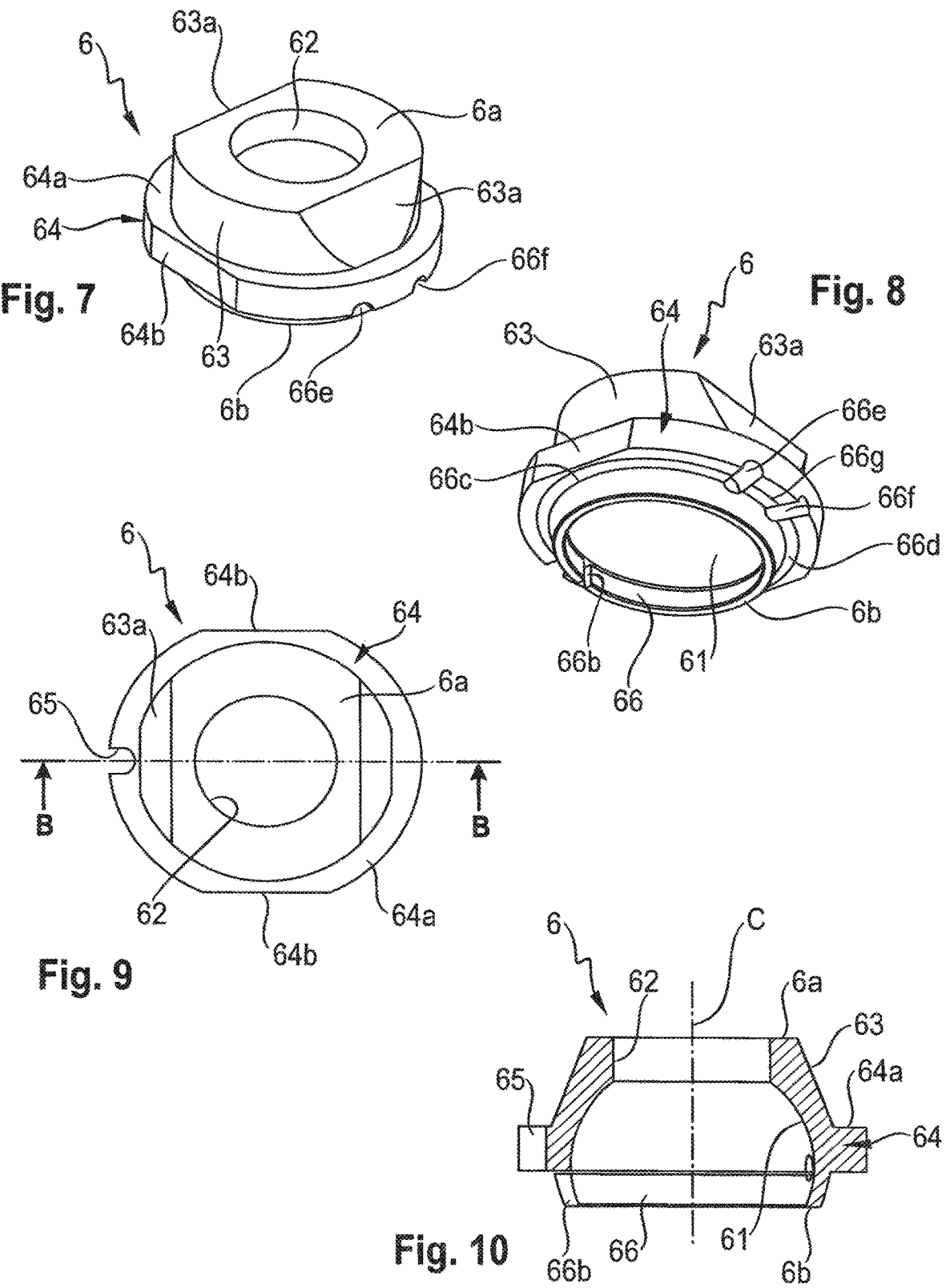
FIG. 7 shows a perspective view from above of a retainer element according to the first embodiment.
FIG. 8 shows a perspective view from a bottom of the retainer element of FIG. 7.
FIG. 9 shows a top view of the retainer element of FIGS. 7 and 8.
FIG. 10 shows a cross-sectional view of the retainer element of FIGS. 7 to 9, the cross-section being taken along line B-B in FIG. 9.

Adjacent to the bottom end 6*b*, the retainer element 6 has the form of a slit ring 66. The slit ring 66 has a substantially conical outer shape that matches the inner shape of the seat portion 54*a* of the accommodation space 54. The inner surface of the slit ring 66 forms a portion of the spherical recess 61, so that the inner surface of the slit ring 66 generates a seat for the head 3, to provide a ball and socket joint between the receiving part 5 and the bone anchoring element 1 when the retainer element 6 is mounted to the receiving part 5. As depicted in FIG. 8, the slit ring 66 is formed by a first vertical slit 66*b* extending from the bottom end 6*b* in a substantially vertical direction. From the vertical slit 66*b* two opposite horizontal slits 66*c*, 66*d* extend circumferentially around the central axis C. The horizontal slits 66*c*, 66*d* end in widened portions 66*e*, 66*f*. Between the end portions 66*e*, 66*f* a connecting portion 66*g* is formed that connects the slit ring 66 to the remainder of the retainer element 6. Hence, the retainer element 6 is a monolithic part including the slit ring 66. The width of the vertical slit 66*b* and of the horizontal slits 66*c*, 66*d* as well as the width of the connecting portion 66*g*, may be selected such that a desired flexibility of the slit ring 66 is obtained. By means of the slit ring 66, the retainer element 6 is configured to be expanded and compressed in a radial direction. As can be seen in particular in FIGS. 8 and 10, the vertical slit is positioned circumferentially at substantially the same position as the U-shaped recess 65, while the connecting portion 66*g* is at a circumferentially opposite position.

As illustrated in FIG. 16, a total axial length of the retainer element 6 when the retainer element 6 is inserted into the receiving part 5 and when the slit ring 66 is seated in the seat portion 54*a* of the receiving part 5 is such that the top end 6*a* of the retainer element 6 is approximately at or slightly above the axial height of the bottom of the U-shaped recess 52. It shall be noted that the retainer element 6 acts also as a pressure element on an inserted head 3, as it not only prevents removal of the head 3, but also exerts pressure to the head 3 from the side and from above.

Figures 11, 12, 13:
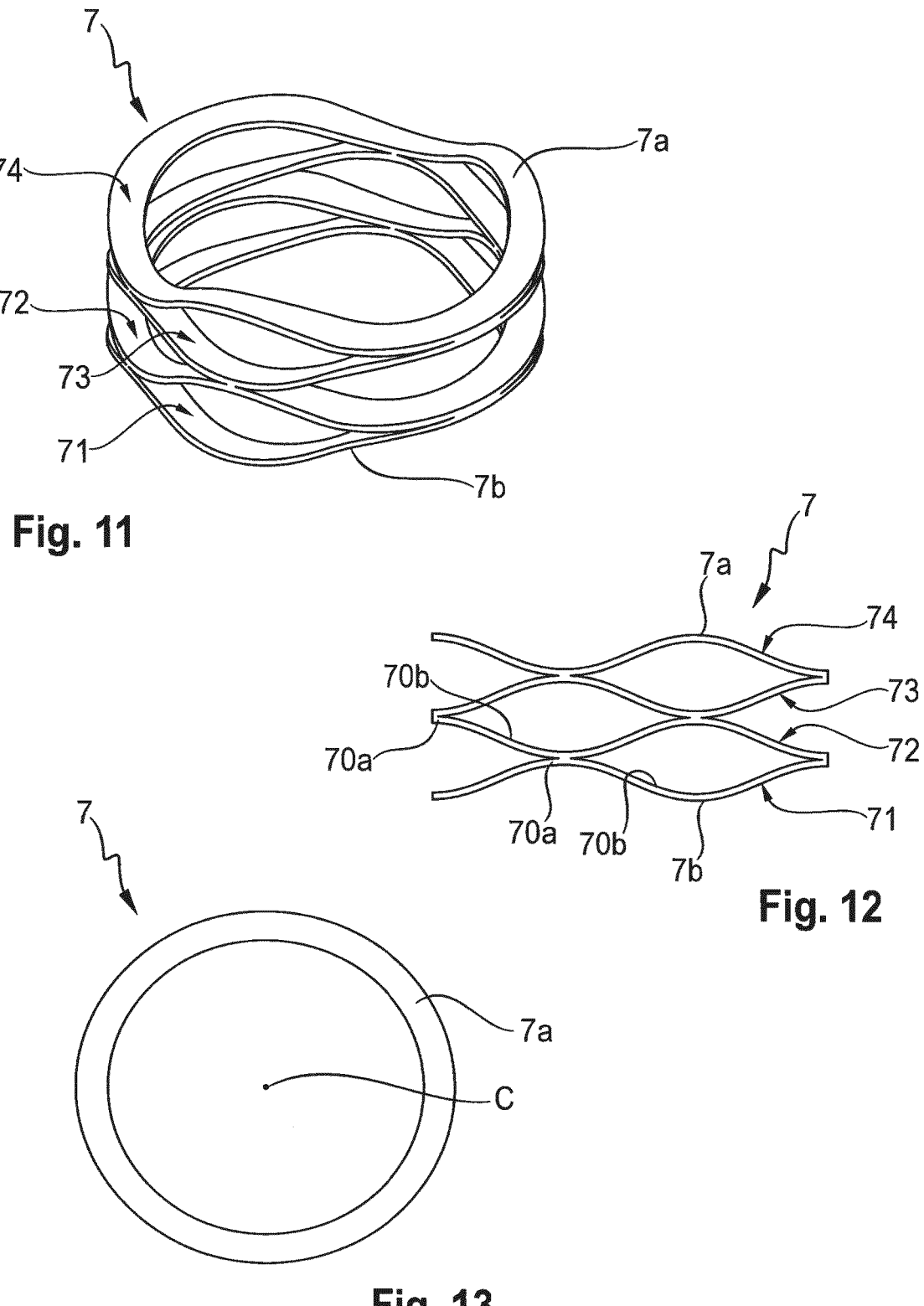
FIG. 11 shows a perspective view from above of a spring element according to the first embodiment.
FIG. 12 shows a side view of the spring element shown in FIG. 11.
FIG. 13 shows a top view of the spring element of FIGS. 11 and 12.

Referring now to FIGS. 11 to 13, the spring element 7 is formed as a wave spring, and includes substantially circular turns each made out of a flat strip, such as a flat wire. A cross-section of the flat strip may be rectangular. In the embodiment shown, the wave spring has four turns 71, 72, 73, 74. However, in other embodiments, a plurality of turns more or less than four turns may be provided. Each turn has a plurality of wave crests 70*a* and a plurality of wave troughs 70*b* that are alternately arranged and that form a ring. The turns 71, 72, 73, 74 that are consecutively stacked in an axial direction around the central axis C are connected to each other, such that adjacent turns offset from one another in a circumferential direction by the length of a crest portion (or a trough portion), as can be seen in particular in FIGS. 11 and 12. This specific shape is known as a crest-to-crest wave spring.

Figures 17, 18, 19:
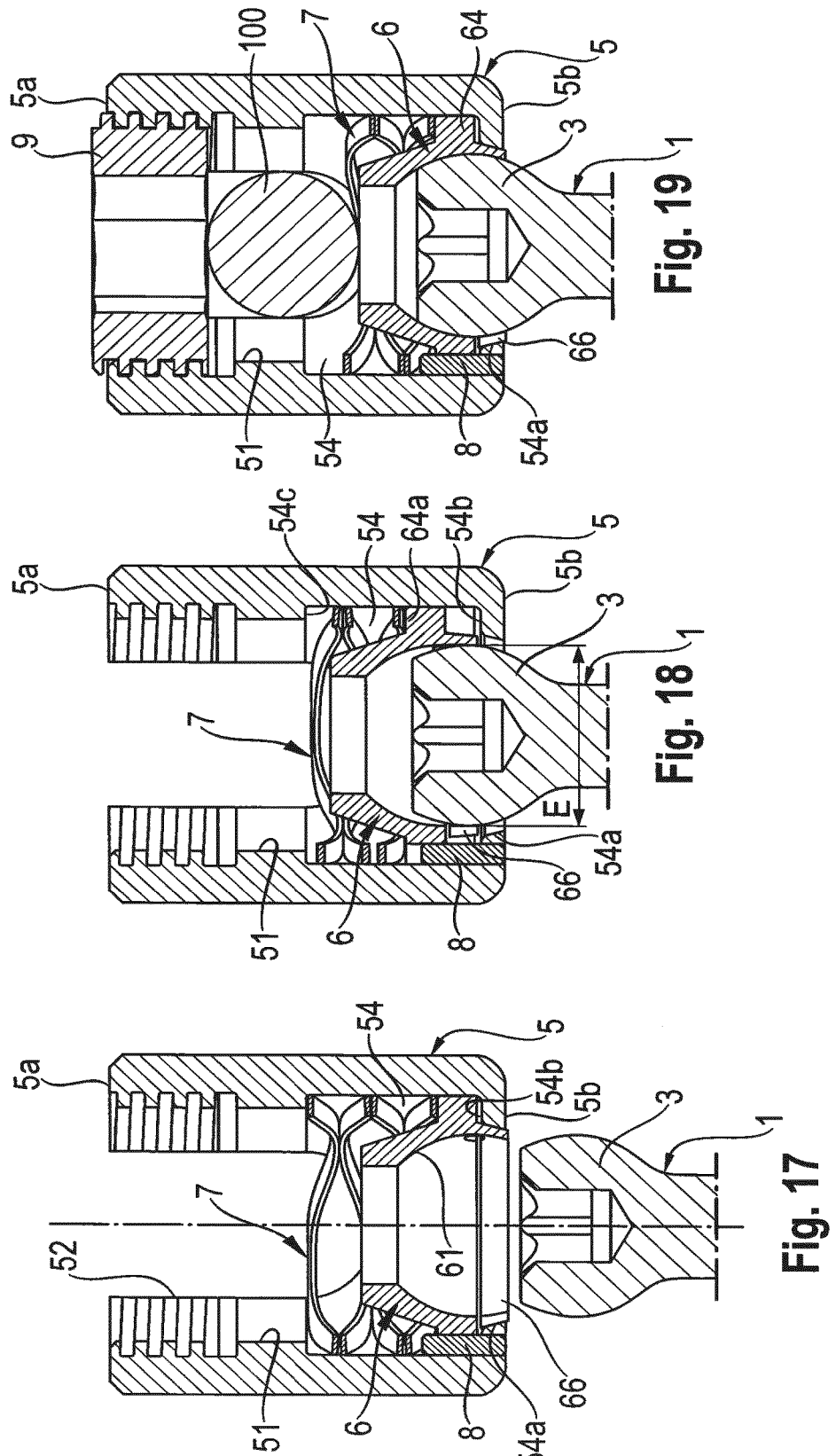
FIGS. 17 to 18 show cross-sectional views illustrating steps of mounting the coupling assembly of the first embodiment to a bone anchoring element.
FIG. 19 shows a cross-sectional view of a fully assembled polyaxial bone anchoring device with the coupling assembly according to the first embodiment, with the inserted bone anchoring element and rod, the cross-section being taken in a plane transverse to an axis of the rod.

The turns of the spring element 7 may each be made out of separate flat strips that may be connected to each other, for example, by welding. Alternatively, the spring element can be made out of a single continuous flat strip that is wound around a central axis, so as to form a wave spring shape. Many modifications are possible. The number of turns, i.e. the axial length of the spring element 7, and various other spring properties can be selected such that a desired compression force and return force can be provided by the spring element 7. The axial length of the spring element is selected such that, as can be seen in FIGS. 17 to 19, the spring element 7 can be positioned onto the first portion 63 of the retainer element 6 and fills the accommodation space 54 between the upper surface 64*a* of the annular edge 64 of the retainer element 6 and the upper edge 54*c* of the accommodation space 54. An outer diameter of the spring element 7 is slightly smaller than an inner diameter of the accommodation space 54.

When the spring element 7 is in the accommodation space 54, the spring element 7 may be in a biased condition so that it exerts a pre-load onto the retainer element 6, but can still be compressed further.

An advantage of a wave spring compared to a helical compression spring is that a wave spring produces the same or similar compression and return force, but can have a shorter axial length than a helical compression spring. As a consequence thereof, the necessary space for the spring element 7 may be smaller or reduced, and/or the travel path for inserting the anchoring element against the spring force can be minimized or reduced.

The bone anchoring device, as a whole or in part, may be made of one or more bio-compatible materials, such as a bio-compatible metal or a metal alloy, for example titanium, stainless steel, a nickel-titanium alloy, for example nitinol, or of bio-compatible plastic materials, such as, for example, polyetheretherketon (PEEK), or of a bio-compatible ceramic material. In particular, it may be contemplated that the spring element 7 is made of a superelastic nickel-titanium alloy or of beta titanium.

The assembly of the coupling assembly will be explained with reference to FIGS. 14 to 16. First, the pin 8 can be inserted beforehand in the through-hole 56 of the receiving part 5. Next, the retainer element 6 is inserted into the receiving part 5 from the top end 5*a*. The retainer element

6 can be inserted in a 90° tilted manner such that its central axis is oriented at 90° with respect to the central axis C of the receiving part. A less than 90° tilted orientation can also be used for insertion, as illustrated. Then, when a portion of the bottom end 6*b* and the annular edge 64 enters the accommodation space 54, the retainer element 6 can be tilted again, so that its central axis becomes coaxial with the central axis C of the receiving part 5. The orientation of the retaining element is such that, as depicted in FIG. 15, the U-shaped axial recess 65 provided at the annular edge 64 engages the pin 8.

When the retainer element 6 is seated with the slit ring 66 in the seat portion 54*a* of the receiving part 5, the spring element 7 is inserted into the accommodation space 54 such that the spring element 7 encircles the upper portion 63 of the retainer element 6 and rests on the upper side 64*a* of the annular edge 64. The top end 7*a* of the spring element 7 abuts against the stop 54*c* provided at the upper side of the accommodating space 54. In this condition, the spring element 7 is somewhat compressed, so that the spring element 7 exerts a biasing force onto the retainer element 6 to hold the slit ring 66 in the seat 54*a*. When the slit ring 66 is placed in to the seat 54*a*, the lower edge 6*b* of the retainer element 6 can project slightly out of the lower opening 55 of the receiving part 5. A portion of the spring element 7 extends above the bottom of the channel 52 of the receiving part 5, so that the spring element 7 can be engaged by the rod 100.

Next, as depicted in FIGS. 17 and 18, the head 3 of the bone anchoring element 1 is inserted through the lower opening 55 into the receiving part 5. As shown in FIG. 18, when the head 3 enters the accommodation space 54 through the lower opening 55, the slit ring 66 is pushed upwards out of the seat 54*a*. Simultaneously, the spring element 7 is compressed by the upward movement of the retainer element 6. In addition, the slit ring 66 is expanded when the head 3 further enters into it. The accommodation space 54 provides space for the expansion after the slit ring 66 is pushed out of the seat 54*a*. When the counterforce exerted by the compressed spring element 7 is greater than the necessary force for expanding the slit ring 66 and for sliding the slit ring 66 over the portion of the head 3 having the largest diameter E, the spring force of the compressed spring element 7 causes the slit ring 66 to snap over the head 3, so that the lower edge 6*b* slides over the region of the head 3 with the largest diameter E. The head 3 can be inserted into the retainer element 6 only to such an extent that the head 3 abuts against the upper portion of the spherical recess 61 of the retainer element 6. The retainer element 6 and the spring element 7 cannot escape through the top end 5*a* of the receiving part 5 because of the stop 54*c* provided in the accommodation space 54.

When the slit ring 66 is positioned below the portion of the head 3 with the greatest diameter E, the head 3 can no longer be pulled-out through the lower opening 55.

The slit ring 66 may have a slight undersize with respect to the size of the head 3 when the slit ring 66 is unbiased, such that when the slit ring 66 encompasses the head 3, a frictional force is exerted onto the head 3. Hence the head 3 may be held by friction within the receiving part 5, and the receiving part 5 can be maintained or held temporarily at a specific angular position with respect to the bone anchoring element 1 before locking of the bone anchoring element 1 relative to the receiving part 5. The spring force exerted by the biased spring element 7 may also contribute to the friction hold of the head 3 in the receiving part 5.

As depicted in FIG. 19, in a next step, the rod 100 is inserted into the U-shaped recess 52 and the locking element 9 is inserted in the receiving part 5. When the locking element 9 is tightened, the rod 100 presses onto the top end 6*a* of the retaining element 6 and also contacts the spring element 7. Final tightening of the locking element 9 locks the slit ring 66 of the retaining element 6 and the head 3 in the receiving part 5. As can be seen in FIG. 19, in the locked condition, the rod 100 also compresses the spring element 7.

In use, the bone anchoring element 1 may be inserted into the bone or into a vertebra prior to mounting the coupling assembly 4. In an alternative manner of use, the bone anchoring element 1 and the coupling assembly 4 are pre-assembled and thereafter inserted into the bone. A plurality of bone anchoring devices can be connected through a stabilization rod 100.

Figures 20, 21:
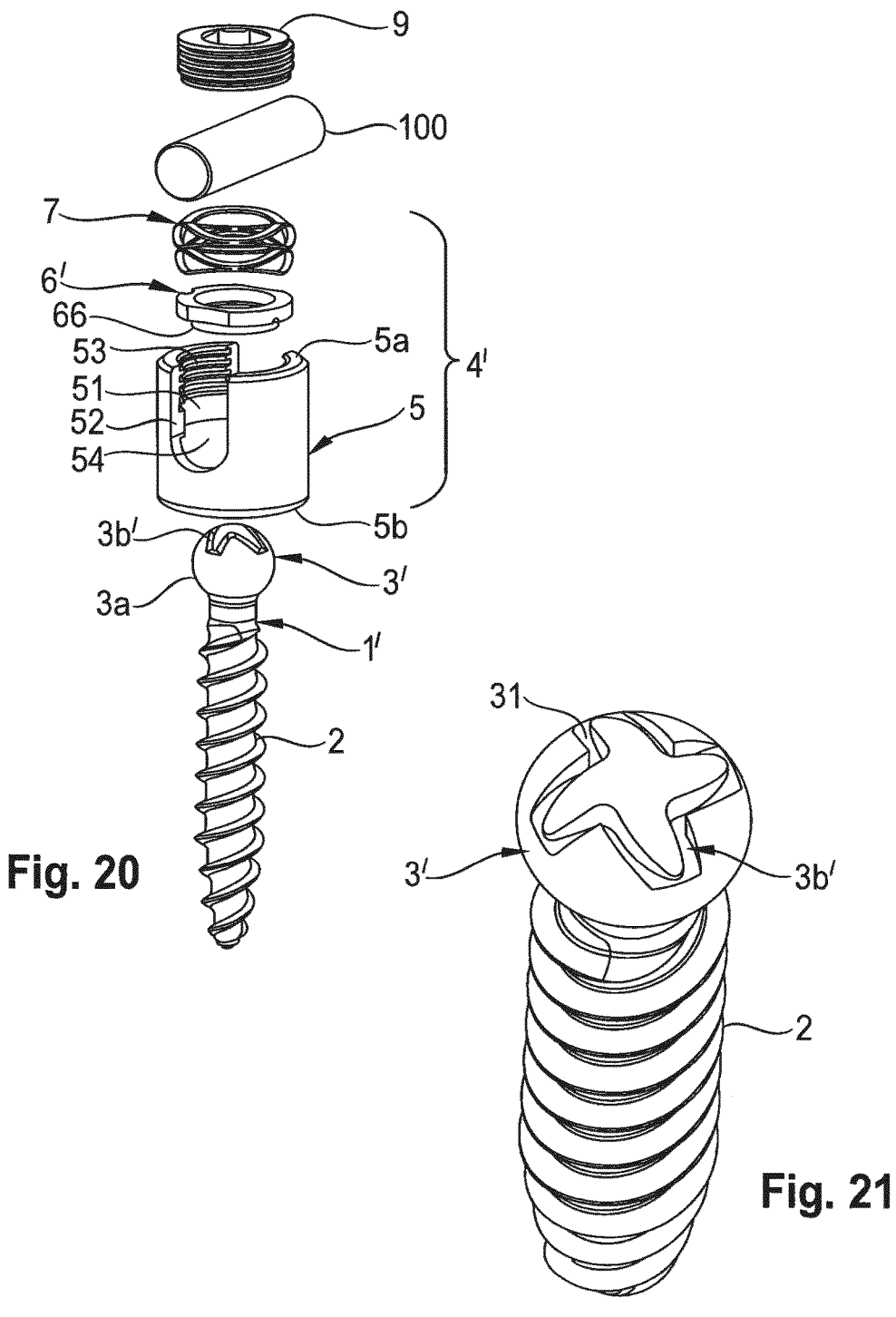
FIG. 20 shows a perspective exploded view of a second embodiment of the polyaxial bone anchoring device, with a second embodiment of the coupling assembly.
FIG. 21 shows a perspective view from above of a bone anchoring element according to the second embodiment.

Referring to FIGS. 20 and 21, a second embodiment of a polyaxial bone anchoring device will be described. The polyaxial bone anchoring device according to the second embodiment differs from the polyaxial bone anchoring device according to the first embodiment in the design of the coupling assembly, and in particular, in the design of the retainer element. All parts that are similar or identical to the previous embodiments are designated with the same reference numerals, and the descriptions thereof will not be repeated.

The coupling assembly 4' includes a retainer element 6', which lacks the first portion 63 of the retainer element 6 of the first embodiment. The retainer element 6' includes an annular portion 64' with a cylindrical inner surface and a slit ring 66 that is identical or similar to the slit ring 66 of the first embodiment. With such a design, the head 3' of the bone anchoring element 1' can protrude out of the top end 6*a* of the retainer element 6'. The size of the retainer element 6' is such that the head 3' protrudes out of the retainer element 6' to an extent that allows the rod 100 to press directly onto the head 3'.

The bone anchoring element 1' according to the second embodiment includes a spherical head 3' that also has a spherical outer surface at a free upper end. In the embodiment, the head as a whole is substantially spherical. The recess 3*b*' for the tool may have wings that extend in a spiral-like manner from a center point of the upper free end. In the embodiment shown, the recess 3*b*' includes four wings that are formed by a groove 31 that forms the outer contour of a cross with arms each bent in a same direction. By means of this, the engagement surface formed by the recess 3*b*' for a tool or driver is enhanced or more robust compared to usual polygon engagements or other recesses or engagements. Therefore, the loads that can be transferred onto the head 3' are higher. Recesses for drivers and corresponding tools with a similar shape are known, for example, under the trademark Mortorq®. It may be contemplated that similar shapes can be used as drive recesses for the head 3'.

Figures 22, 23:
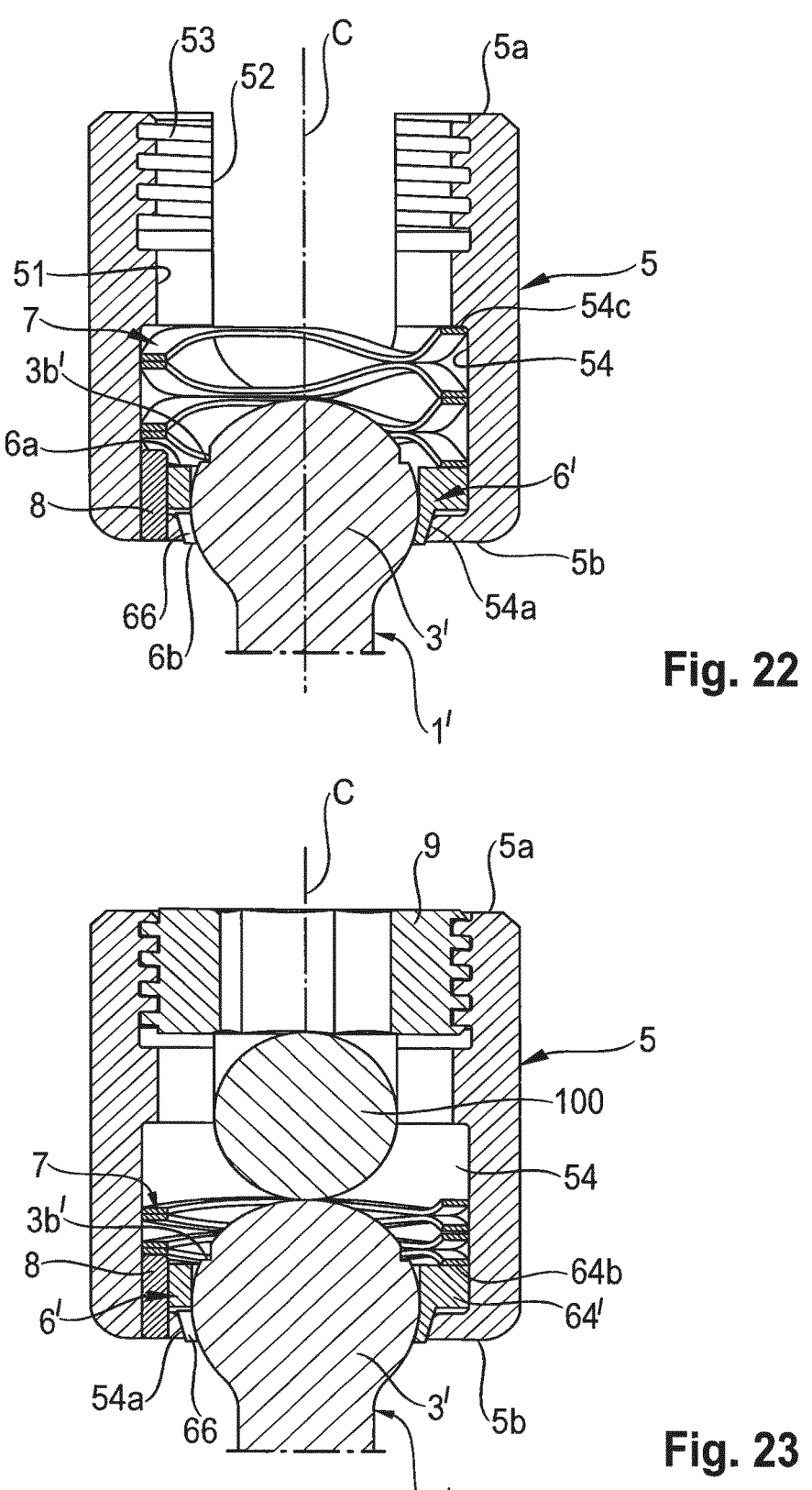
FIG. 22 shows a cross-sectional view of the second embodiment of the polyaxial bone anchoring device, wherein the bone anchoring element is inserted into the coupling assembly, the cross-section being taken in a plane perpendicular to a rod channel axis.
FIG. 23 shows a cross-sectional view of a fully assembled polyaxial bone anchoring device according to the second embodiment, with an inserted and fixed rod.

As depicted in FIG. 22, when the head 3' has entered the receiving part 5 and the retainer element 6', the upper portion of the head 3' including the drive recess 3*b*' protrudes out from the top end 6*a* of the retainer element 6'. Also in this embodiment, the head 3 cannot be pulled out through the lower opening 55 once the retainer element 6' is seated in seat 54*a* of the receiving part 5. The spring element 7 projects into the channel 52 for the rod 100. Hence, the rod 100 engages the spring element 7 when it is inserted into the recess 52. When the rod 100 is moved down via the locking element 9, as depicted in FIG. 23, the rod 100 compresses the spring element 7, which in turn urges the retainer element 6' into the seat 54*a* of the receiving part 5. Finally, the rod 100 presses onto the upper surface of the head 3', whereby the head 3' is pressed into the seat provided by the slit ring 66 of the retainer element 6'. Because of the spherical shape of the head 3', sufficient pressure is exerted onto the head 3' in both non-pivoted and pivoted states of the bone anchoring element 1' relative to the receiving part 5.

The other steps of mounting the retainer element 6' to the receiving part 5 are the same as or similar to the first embodiment.

Figures 24, 25:
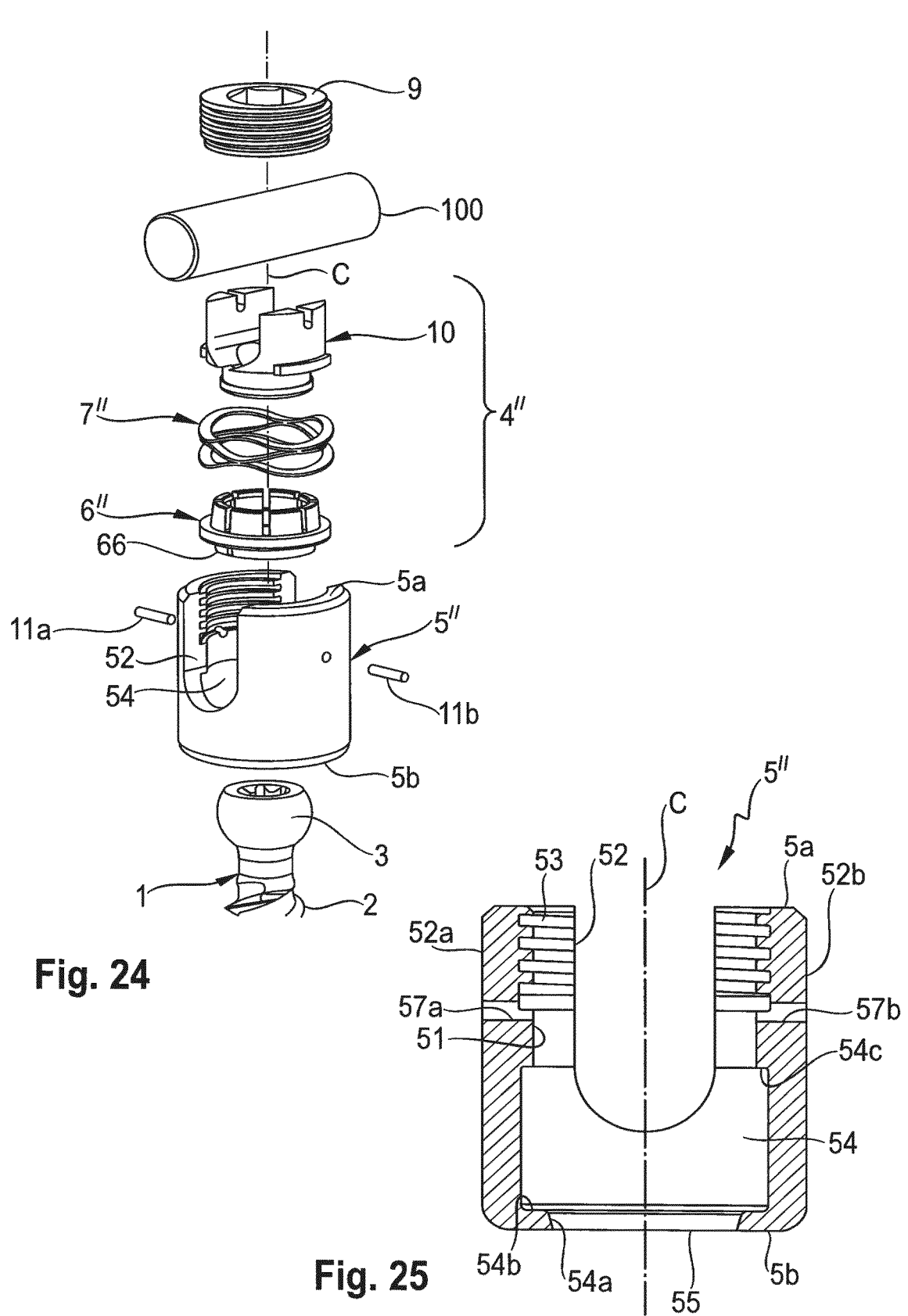
FIG. 24 shows a perspective exploded view of a third embodiment of the polyaxial bone anchoring device, with a third embodiment of the coupling assembly.
FIG. 25 shows a cross-sectional view of a receiving part according to the third embodiment, the cross-section being taken in a plane perpendicular to a rod channel axis.

A third embodiment of a polyaxial bone anchoring device including a coupling assembly will be described with reference to FIGS. 24 to 39. First, as can be seen in FIG. 24, the coupling assembly 4" includes a receiving part 5", a retainer element 6", a spring element 7", and additionally a pressure element 10 for exerting pressure onto the head 3 of the bone anchoring element 1. It shall be noted that in this embodiment the bone anchoring element 1 is the same as or similar to the bone anchoring element 1 of the first embodiment. However, embodiments of the invention should not be limited thereto, and another bone anchoring element, for example, that of the second embodiment, can also be used. Parts and portions of the third embodiment that are identical or similar to that of the first or second embodiments are marked with the same reference numerals, and the descriptions thereof will not be repeated.

The receiving part 5" of the third embodiment is depicted in a cross-sectional view taken in a place perpendicular to an axis of the rod recess 52 in FIG. 25. The receiving part 5" lacks the through-hole 56 for the pin 8 at the bottom end 5*b*. For the purpose of holding a pressure element 10 inside the receiving part 5" and for preventing rotation of the inserted pressure element 10, the receiving part 5" includes two transverse pin holes 57*a*, 57*b* that are positioned in a circumferential direction substantially at centers of the legs 52*a*, 52*b*. The pin holes 57*a*, 57*b* are configured to accommodate pins 11*a*, 11*b* in a press-fit manner. The length of the pins 11*a*, 11*b* is such that the pins 11*a*, 11*b* can protrude into the bore 51 of the receiving part 5" to engage the pressure element 10. The axial position of the through-holes 57*a*, 57*b* is such that, as depicted for example in FIG. 36, the pressure element 10 is held by the pins 11*a*, 11*b* at its upper end, to be described in greater detail below.

The retainer element 6" differs from the retainer elements of the first and the second embodiments in that there is a portion 63" adjacent to an upper surface 64*a* of the annular outwardly protruding edge 64" that includes a plurality of circumferentially arranged upstanding slightly resilient wall portions 63*a* that are separated by axial slots so as to provide elasticity. Each wall portion 63*a* has an inwardly protruding edge 63*b*. The inwardly protruding edges 63*b* are configured to engage a portion of the pressure element 10 so that the pressure element 10 and the retainer element 6" can be coupled together. An inner and an outer surface of the wall portions 63*a* is each substantially conical, tapering and narrowing towards the top end 6*a*.

Figures 26, 27, 28, 29:
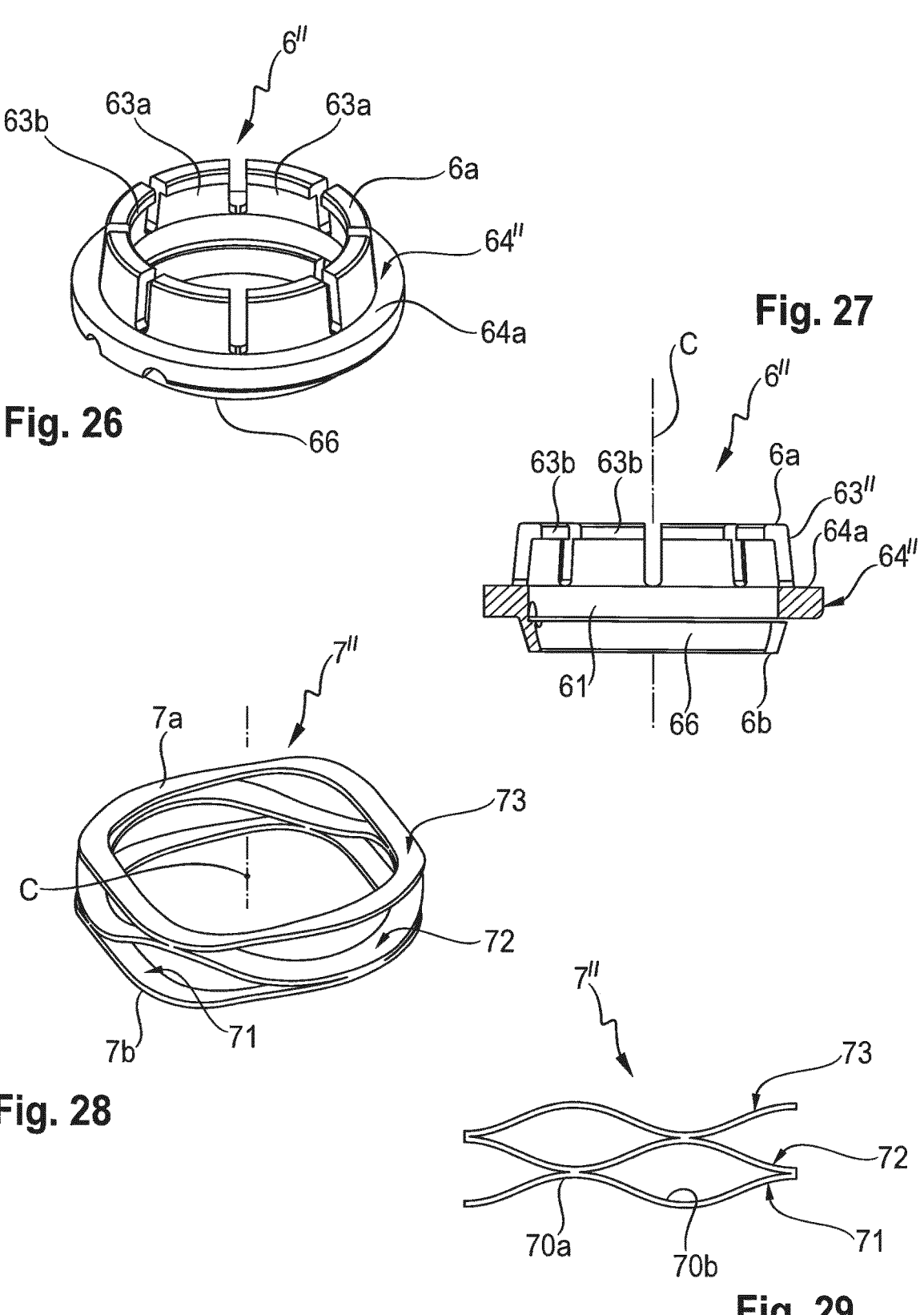
FIG. 26 shows a perspective view from above of a retainer element according to the third embodiment.
FIG. 27 shows a cross-sectional view of the retainer element shown in FIG. 26.
FIG. 28 shows a perspective view from a top of a spring element according to the third embodiment.
FIG. 29 shows a side view of the spring element of FIG. 28.
Figures 30, 31, 32, 33:
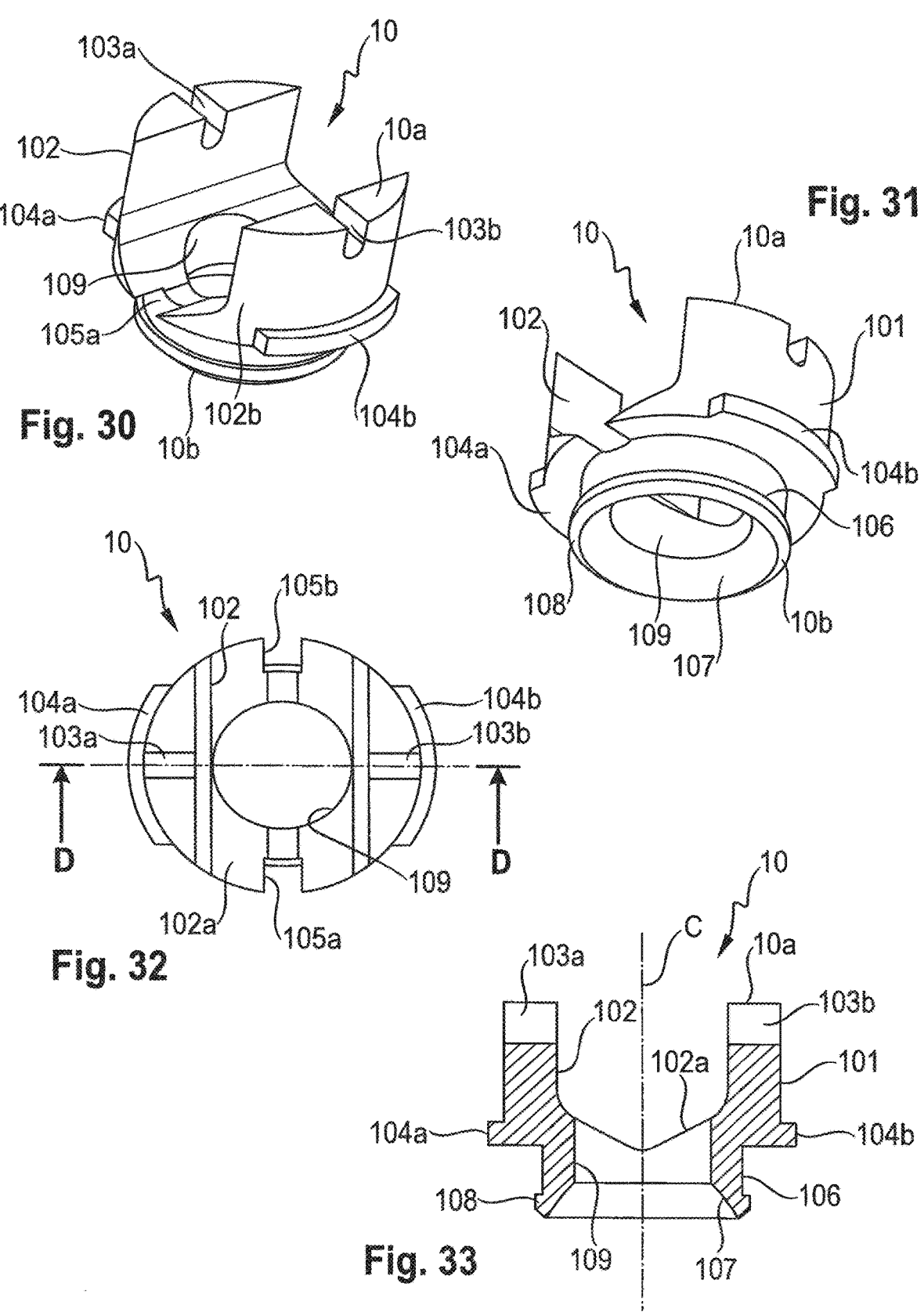
FIG. 30 shows a perspective view from above of a pressure element according to the third embodiment.
FIG. 31 shows a perspective view from a bottom of the pressure element shown in FIG. 30.
FIG. 32 shows a top view of the pressure element of FIGS. 30 and 31.
FIG. 33 shows a cross-sectional view of the pressure element shown in FIGS. 30 to 32, the cross-section being taken along line D-D in FIG. 32.

The annular edge 64" lacks the recess of the retainer element for receiving the pin in the first embodiment, as there is no pin in the third embodiment for holding the retainer element. The slit ring 66 is the same as or similar to the slit ring 66 from the first and second embodiments. As depicted in FIGS. 28 and 29, the spring element 7" is also a wave spring, preferably of the type of a crest-to-crest wave spring. The spring element 7" has three turns in the embodiment shown, but the number of turns is not limited to three, and the spring element in other embodiments can have two or more than three turns, depending on the available space in the accommodation space 54 and on the spring characteristics of the spring element. An inner and an outer diameter of the spring element 7" is such that the spring element 7" is configured to be supported on the upper side 64*a* of the annular edge 64" of the retainer element 6" and to extend around the first portion 63" having the flexible wall portions 63*a*.

Figures 34, 35, 36:
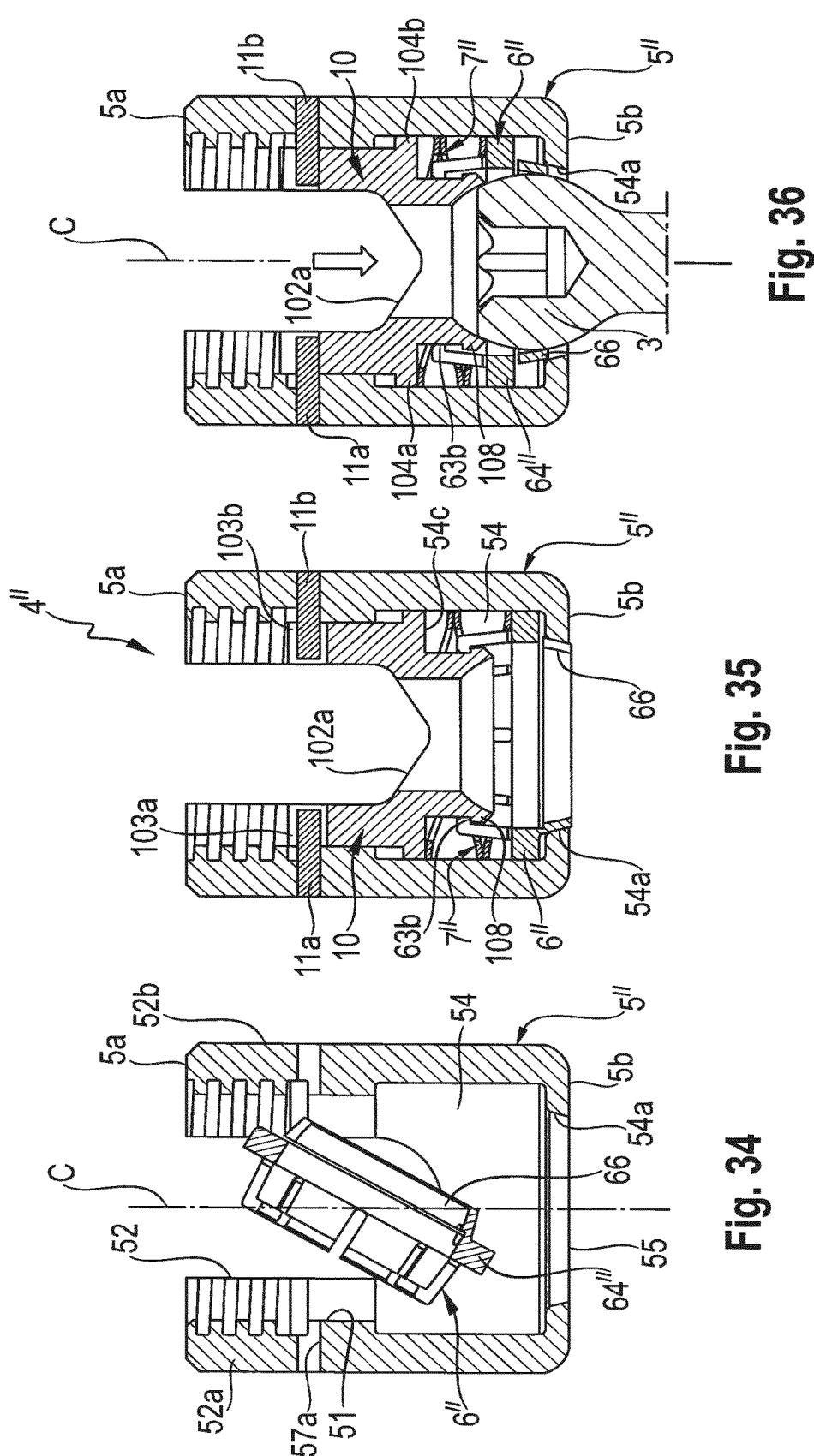
FIGS. 34 to 35 show cross-sectional views illustrating steps of assembling the coupling assembly according to the third embodiment.
FIG. 36 shows a cross-sectional view of a step of mounting the coupling assembly of the third embodiment to a bone anchoring element.

The pressure element 10 has a first end or top end 10*a* and a second end or bottom end 10*b*. Adjacent to the top end 10*a* there is a substantially cylindrical section with a first outer diameter that is only slightly smaller than the inner diameter of the bore 51 of the receiving part 5" so that the first portion 101 can be slidingly arranged in the bore 51. Adjacent to the top end 10*a* there is also a transverse recess 102 with substantially parallel side walls and a substantially V-shaped bottom 102*a* that forms a channel for receiving the rod 100, where the rod axis is perpendicular to the central axis C. The V-shaped bottom 102*a* is configured to support rods of different diameter. By the recess 102, two upstanding legs 102*b*, 102*c* are formed that are provided at their top side with smaller U-shaped recesses 103*a*, 103*b*, respectively, which are open to the top end 10*a* and which extend transverse to an axis of the channel. The recesses 103*a*, 103*b* are configured to receive a portion of the pins 11*a*, 11*b*, respectively, as can be seen in FIGS. 35 and 36, for example. Each of the legs 102*b*, 102*c*, respectively has an outwardly projecting flange 104*a*, 104*b* that is arranged substantially at the height of the V-shaped bottom 102*a* and that extends in a circumferential direction around a portion of each respective leg 102*b*, 102*c*.

At either end of the bottom of the channel 102 for the rod 100, recesses 105*a*, 105*b* are provided that allow for insertion of the pressure element 10 when the pins 11*a*, 11*b* are already mounted into the pin holes 57*a* and 57*b* of the receiving part 5".

The pressure element 10 further includes, adjacent to the bottom end 10*b*, a second portion 106 with a smaller diameter compared to the first portion 101. The second portion 106 is substantially cylindrical and has a spherical segment-shaped recess 107 adjacent to the bottom end 10*b*. The spherical recess 107 is configured to exert pressure onto the head 3 of the bone anchoring element 1. An outwardly protruding edge 108 is provided at the bottom end 10*b* for engaging the inwardly protruding edges 63*b* of the retainer element 6" to couple the pressure element 10 to the retainer element 6". The edge 108 has a chamfered lower side for facilitating insertion of the second portion 106 into the retainer element 6". Furthermore, the pressure element 10 has a coaxial bore 109 for providing access to the head 3 of the bone anchoring element 1 with a tool (not shown).

The assembly of the coupling assembly 4" will be explained with reference to FIGS. 34 and 35. The retainer element 6" is inserted from the top end 5*a* of the receiving part 5" in a tilted manner. When the retainer element 6" has reached the accommodation space 54, the retainer element 6" is tilted back and placed onto the bottom of the accommodation space 54, with the slit ring 66 being in the seat 54*a*.

When the retainer element 6" has been inserted into the receiving part 5", the spring element 7" is also inserted from the top end 5*a* of the receiving part 5" and placed on top of the retainer element 6" so that the spring element 7" rests on the annular edge 64".

Next, the pressure element 10 is inserted into the receiving part 5" from the top end 5*a*. As the pins 11*a*, 11*b* may already be received in the pin holes 57*a*, 57*b* of the receiving part 5", the pressure element 10 can be inserted in a 90° rotated position, so that the recess 102 is oriented at 90° with respect to the U-shaped recess 52 of the receiving part 5" and the flanges 104*a*, 104*b* are aligned with the U-shaped recess 52. In this configuration, the pins 11*a*, 11*b* can pass through the slits 105*a*, 105*b*. When the pressure element 10 enters the upper portion 63" of the retainer element 6", the flexible wall portions 63*a* are deflected slightly outward to allow the insertion of the bottom end 10*b* of the pressure element 10, until the inwardly protruding edge 63*b* of the retainer element 6" snaps behind or over the outward edge 108 of the lower portion of the pressure element 10. Once the flanges 104*a*, 104*b* have entered the accommodation space 54, the pressure element 10 can be rotated so that the channel 102 of the pressure element 10 and the U-shaped recess 52 of the receiving part 5" are aligned. Rotation may only be possible when the top end 10*a* of the pressure element 10 is below the pins 11*a*, 11*b*.

After alignment of the pressure element 10, the pins 11*a*, 11*b* are received in the U-shaped recesses 103*a*, 103*b*, respectively, of the pressure element 10. The bottom of the U-shaped recesses 103*a*, 103*b* form an abutment for pressure element 10 and prevent escaping of the pressure element 10 through the top end 5*a* of the receiving part 5". In the preassembled state of the coupling assembly 4", as depicted in FIG. 35, the spring element 7" is slightly pre-compressed.

Figures 37, 38, 39:
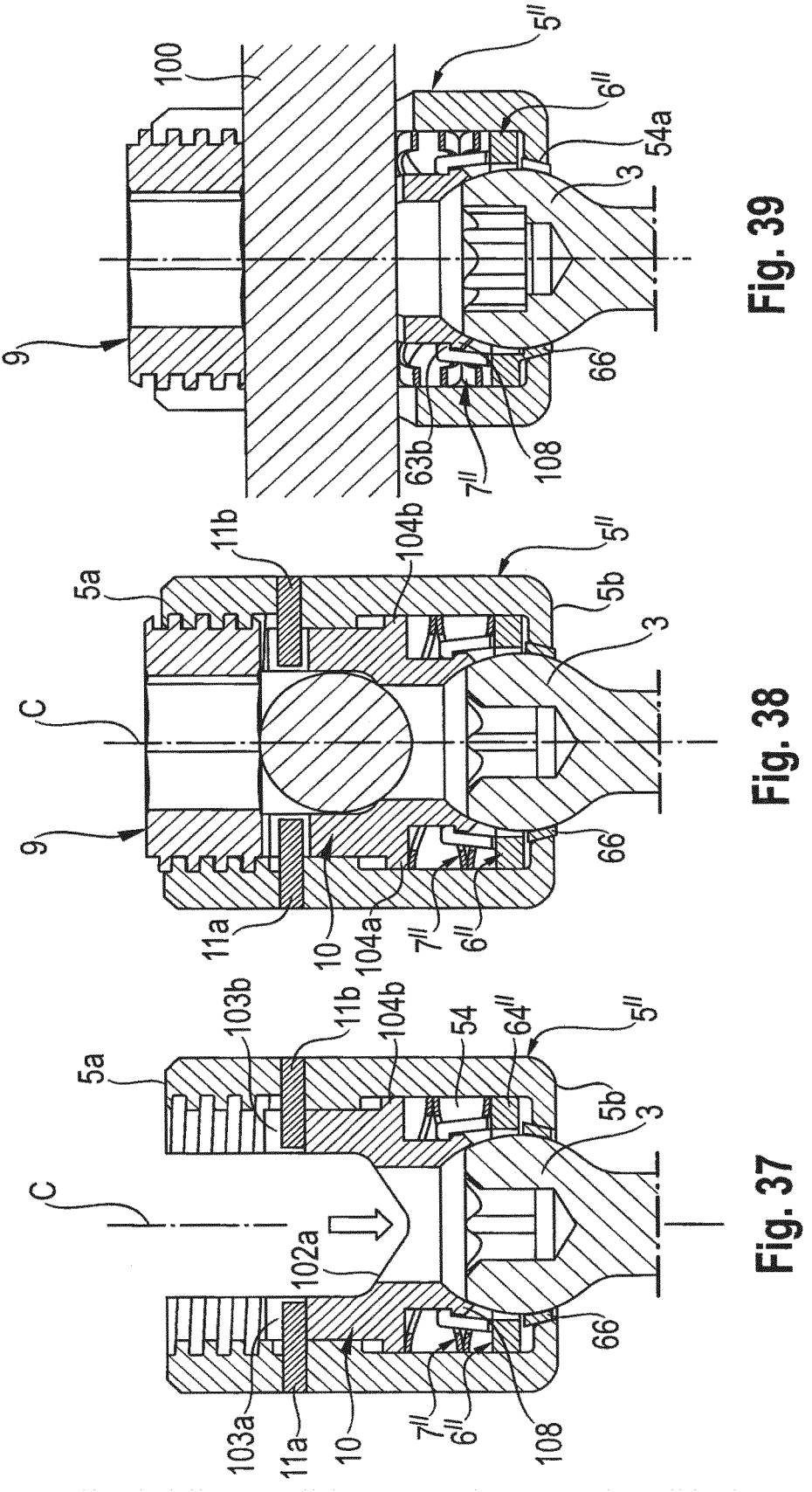
FIG. 37 shows a cross-sectional view of a fully assembled polyaxial bone anchoring device according to the third embodiment.
FIG. 38 shows a cross-sectional view of the polyaxial bone anchoring device of FIG. 37 with an inserted and fixed rod, wherein the cross-section is taken in a plane transverse to a rod axis.
FIG. 39 shows a cross-sectional view of the polyaxial bone anchoring device according to the third embodiment, wherein the cross-section is taken in a plane containing the rod axis.

The mounting of the coupling assembly 4" to the bone anchoring element 1 is shown in FIGS. 36 and 37. As in the first embodiment, the head 3 enters through the lower opening 55 into the retainer element 6", and therefore into the accommodation space 54. The slit ring 66 is pushed out of seat 54*a* and the retainer element 6" is moved upward, whereby the contacting surfaces of the outer rim 108 of the pressure element 10 and of the inwardly protruding edges 63*b* of the retainer element 6" disengage. During upward movement of the retainer element 6", the spring element 7" is compressed, whereby the spring element 7" abuts against the lower side of the flanges 104*a*, 104*b* and/or other portions of the lower side of the first portion 101 of the pressure element 10. The upward movement of the pressure element 10 is limited by the pins 11*a*, 11*b*.

During the insertion of the head 3 into the retainer element 6", the slit ring 66 expands. As soon as the counterforce exerted by the compressed spring element 7" is greater than the necessary force for expanding the slit ring 66 and for sliding the slit ring 66 over the portion of the head 3 with the largest diameter E, the spring force of the compressed spring element 7" causes the slit ring 66 to snap over the head 3 so that the lower edge 6*b* slides over the region with the largest diameter E. The head 3 can be inserted until it abuts against the spherical recess 107 of the pressure element 10. When the spring force shifts the retainer element 6" downward, the inwardly protruding edges 63*b* and the outward rim 108 engage again.

The pre-stress exerted by the spring element 7" and/or a slight undersize of the slit ring 66 compared to the size of the head 3 leads to a frictional hold of the head 3 in the receiving part 5" before finally locking the head 3. Also, when the slit ring 66 enters the seat 54*a* again, a removal of the head 3 from the receiving part 5" may no longer be possible.

Finally, as can be seen in FIGS. 38 and 39, the rod 100 is inserted and pressed down by tightening the locking element 9 in the receiving part 5". The pressure exerted by the pressure element 10 onto the head 3 further presses the slit ring 66 into the seat 54*a*, and final tightening locks the head 3 and the retainer element 6" in the receiving part 5".

Further modifications of the disclosed embodiments may be contemplated. For example, for the bone anchoring element, various different kinds of anchoring elements can be used and combined with the receiving part. The anchoring elements may be, for example, screws with different lengths, screws with different diameters, cannulated screws, screws with different thread forms, nails, hooks, etc. For some anchoring elements, the head and the shank may also be separate parts that can be connected to each other.

Some possible modifications of the receiving part may include, for example, instead of the U-shaped recess being perpendicular to the central axis, a recess for the rod may be inclined, open to the side, or in the form of a closed channel. Other kinds of locking devices including outer nuts, outer caps, bayonet locking devices, or others can also be utilized. In particular, a two-part locking device that includes a first locking element that exerts pressure via the pressure element onto the head and a second locking element that exerts pressure only onto the rod to lock the head and the rod independently may also be used. In some embodiments, the inner surface portion of the pressure member that contacts the head may not necessarily be spherically-shaped. The inner surface portion may have any other shape that is suitable to exert pressure onto the head. Also, the design of the pressure element can be different and is not limited to the specific design shown in the third embodiment.

Instead of the pin for retaining the pressure element and for aligning the pressure element with respect to the channel of the receiving part for receiving the rod, other retaining mechanisms can be used.

In some embodiments, the head of the bone anchoring element is not rotationally symmetric. For example, the head may have two opposite flat surface portions between two spherically-shaped outer surface portions, to achieve pivoting in only one plane.

Instead of the slit ring, a plurality of vertically extending slits or a combination of substantially vertically and substantially horizontally extending slits may be provided.

The seat for the slit ring and the outer surface of the slit ring need not be conical. Any shape that provides for safe holding of the slit ring may be contemplated, such as, for example, a spherical shape.

For the spring element, other spring elements can be used. For example, a helical spring encircling the central axis may be used. In addition, other spring elements like elastomeric cushions may be contemplated.

It shall be noted that parts of the different embodiments described may also be mixed among each other or exchanged, so that a variety of further embodiments can be generated.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A coupling assembly for coupling a rod to a bone anchoring element, the coupling assembly comprising:
a receiving part having a first end, a second end below the first end, a central axis extending through the first end and the second end, a recess at the first end for receiving the rod, and an accommodation space at the second end for accommodating a head of the bone anchoring element;
a seat positionable at least partially in the accommodation space, the seat comprising an upwardly facing surface configured to contact and exert an upwardly directed pressure on the head;

a pressure element separable from the seat and positionable at least partially in the accommodation space, the pressure element comprising a downwardly facing surface configured to contact and to exert a downwardly directed pressure on the head for locking the head in the receiving part; and
a spring separable from the seat and the pressure element, wherein the spring is configured to extend uninterruptedly around a majority of a circumference around the central axis and to contact the seat in the receiving part;
wherein when the pressure element, the seat, and the spring are in the receiving part, the spring is configured to extend to an axial position above a bottom of the pressure element, and to have an outer width that is as wide as maximum outer widths of the pressure element and the seat, respectively.

2. The coupling assembly of claim 1, wherein the spring is configured to extend uninterruptedly for the entire circumference around the central axis.

3. The coupling assembly of claim 1, wherein the accommodation space forms an opening at the second end of the receiving part sized to permit insertion of the head of the bone anchoring element therethrough, and wherein the seat is radially expandable to facilitate passing of a greatest diameter of the head therethrough.

4. The coupling assembly of claim 1, wherein at least part of the spring is movable axially in the receiving part.

5. The coupling assembly of claim 1, wherein an upper surface of the spring is configured to abut against the pressure element in the receiving part.

6. The coupling assembly of claim 1, wherein the spring is configured to extend to an axial position below the bottom of the pressure element.

7. The coupling assembly of claim 1, wherein an inner width of the spring is as wide as an outer width of the pressure element, to facilitate positioning of the spring around at least part of the pressure element.

8. The coupling assembly of claim 1, wherein the seat comprises an expandable portion, and wherein an inner width of the spring is as wide as an outer width of the expandable portion of the seat.

9. A bone anchoring device for coupling a rod to a bone, the bone anchoring device comprising:
a bone anchoring element comprising a shank for anchoring to the bone and a head;
a receiving part having a first end, a second end below the first end, a central axis extending through the first end and the second end, a recess at the first end for receiving the rod, an accommodation space for accommodating the head of the bone anchoring element, and an opening at the second end sized to facilitate insertion of the head therethrough into the accommodation space;
a seat positionable at least partially in the accommodation space, the seat comprising an upwardly facing surface engageable with the head to hold the head in the receiving part;
a rod contacting element separable from the seat, the rod contacting element comprising a rod contacting surface configured to extend into the recess of the receiving part to engage the rod; and
a third element separable from the seat and the rod contacting element;
wherein each of the seat, the rod contacting element, and the third element is insertable from the first end of the receiving part into the receiving part to a configuration where the third element is directly engageable with both the seat and the rod contacting element, and wherein when the seat, the rod contacting element, and the third element are assembled to the receiving part, the head is insertable through the opening at the second end of the receiving part into the accommodation space.

10. The bone anchoring device of claim 9, wherein the third element comprises a spring configured to extend uninterruptedly around a majority of a circumference around the central axis.

11. The bone anchoring device of claim 9, wherein the rod contacting element further comprises a downwardly facing surface configured to contact and exert a downwardly directed pressure on the head for locking the head in the receiving part.

12. The bone anchoring device of claim 9, wherein the rod contacting element is insertable downwardly from the first end of the receiving part past an abutment of the receiving part, and is configured to be restricted from being removed from the first end of the receiving part by the abutment.

* * * * *